United States Patent [19]

Twisselmann

[11] Patent Number: 4,834,519

[45] Date of Patent: May 30, 1989

[54] LOAD-LOCKING JOINT, PARTICULARLY FOR SURGERY MICROSCOPES AND SUSPENSION MOUNT CONSTRUCTED FOR THE SAME

[76] Inventor: Lorenz Twisselmann, Hudenkamp 4, D-2081 Prisdorf, Fed. Rep. of Germany

[21] Appl. No.: 807,561

[22] Filed: Dec. 11, 1985

[30] Foreign Application Priority Data

Apr. 18, 1985 [DE] Fed. Rep. of Germany ... 8511531[U]

[51] Int. Cl.$^4$ .................. G02B 21/24; G02B 7/02; F16C 11/06
[52] U.S. Cl. ..................... 350/522; 350/256; 403/90
[58] Field of Search ............ 403/56, 90, 122; 350/507, 522, 245, 246, 256

[56] References Cited

U.S. PATENT DOCUMENTS

| | | | |
|---|---|---|---|
| 2,089,439 | 8/1937 | Silberstein | 403/122 |
| 2,161,718 | 6/1939 | Miller | 403/90 |
| 2,696,392 | 12/1954 | Case | 403/122 |
| 2,967,458 | 1/1961 | Stone | 350/522 |

FOREIGN PATENT DOCUMENTS

| | | | |
|---|---|---|---|
| 722451 | 12/1931 | France | 403/90 |
| 291547 | 3/1927 | United Kingdom | 403/90 |
| 449488 | 6/1936 | United Kingdom | 403/90 |

OTHER PUBLICATIONS

Fundamentals of Physics, Halliday & Resnick, Second Edition, 1981, pp. 79–82.

Primary Examiner—John K. Corbin
Assistant Examiner—Ronald M. Kachmarik
Attorney, Agent, or Firm—Antonelli, Terry, Wands

[57] ABSTRACT

The load-locking joint, which is particularly suitable as a suspension mount for surgery microscopes, comprises a joint ball mounted in a housing and having a shaped-on hinge pin or rod, whose free mobility can be inhibited in its mount by mechanical clamping elements. The self-locking action is brought about in that the clamping elements engage on the spherical surface of the ball and during the rotation of the joint ball are carried along on said side, but are supported on a fixed abutment on the other side, the length between the point on the joint ball and the support point increasing with a slope, whose tangent is smaller than the friction coefficient.

17 Claims, 4 Drawing Sheets

Fig. 1a PRIOR ART   Fig. 1b PRIOR ART
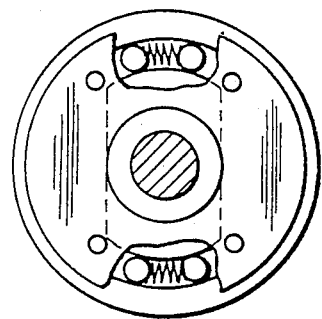
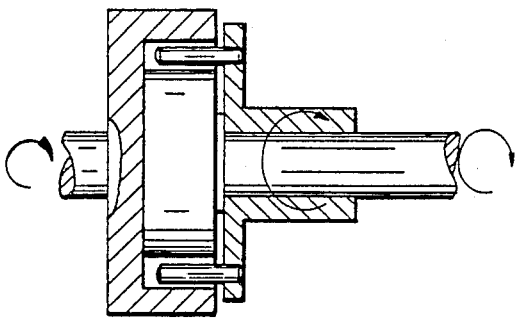
Fig. 2 PRIOR ART
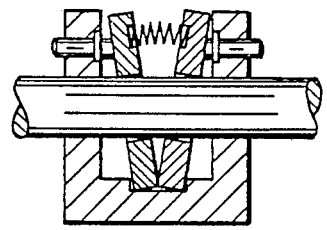
Fig. 3
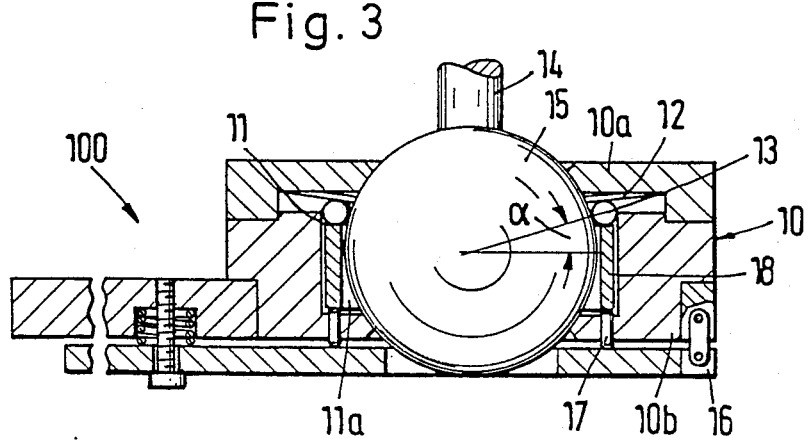

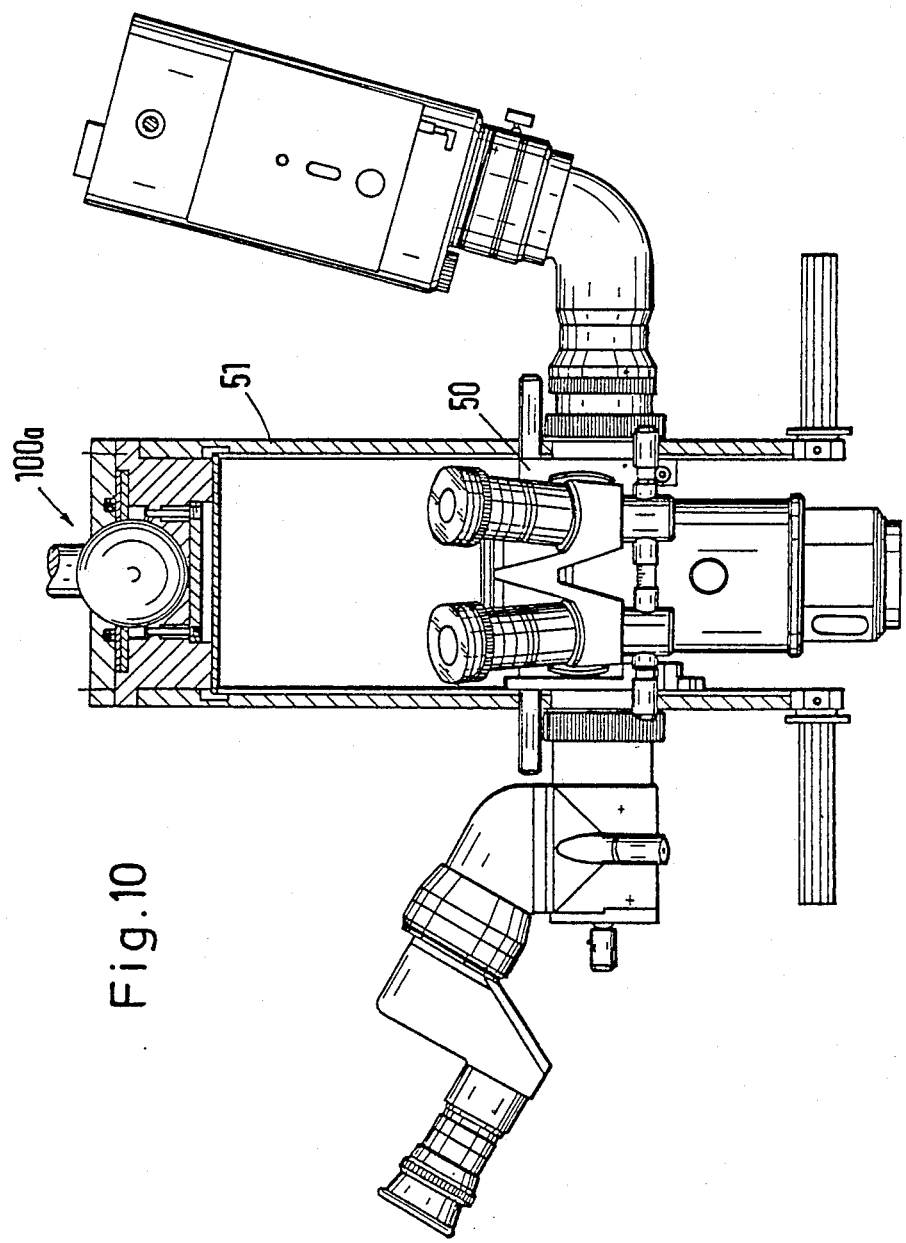

ND-LOCKING JOINT, PARTICULARLY FOR
SURGERY MICROSCOPES AND SUSPENSION
MOUNT CONSTRUCTED FOR THE SAME

BACKGROUND OF THE INVENTION

The present invention relates to a load-locking joint, particularly for surgery microscopes and to a suspension mount constructed for the same.

Load-locking swivel and thrust joints, as shown in FIGS. 1a, 1b and 2 are known. The function of these joints is to act in only a single plane or about an axis.

SUMMARY OF THE INVENTION

The problem of the invention is to provide a spatially acting, load-locking joint, particularly for surgery microscopes, which can be economically manufactured without great technical expenditure and which can be used as a surgery microscope suspension mount.

For the solution of this problem, a load-locking joint, particularly for surgery microscopes, is proposed which, according to the invention, is constructed in such a way that the joint comprises a joint ball mounted in a housing with a shaped-on hinge rod or pin, whose free mobility in its mounting can be inhibited by mechanical clamping elements.

In the case of a load-locking ball joint constructed in this way, self-locking is brought about in that the clamping elements engage on the spherical surface of the joint ball and, when the clamping elements are in the form of pins or disk segments, one end of the pin or disc segment is moved along on this surface during the rotation of the joint ball, while the other end is supported on a fixed abutment, the distance between the point on the joint ball and the support point increases with a slope, whose tangent is less than the friction coefficient.

The load-locking ball joint is used if a once set position of a part or device is to be maintained and if there is to be a possibility of easy spatial adjustability on removing the load-locking action.

The load-locking ball joint has a simple construction and can be economically manufactured. The load-locking ball joint is particularly suitable for use as a suspension mount for surgery microscopes. The operating members for the unlocking of the self-locking action then are fitted in the vicinity of the operating area alongside the microscope objective and are simultaneously used for pivoting the microscope into the correct working position.

Further advantageous developments of the invention are to provide a novel load-locking ball joint which is especially adapted for use as a surgery microscope suspension mount.

BRIEF DESCRIPTION OF THE DRAWINGS

The invention is described in greater detail hereinafter relative to non-limitative embodiments and the attached drawings, wherein:

FIGS. 1a and 1b depict a vertical longitudinal section, a prior art load-locking swivel joint in a view from the front with parts of the cover removed.

FIG. 2 is a vertical longitudinal section through a prior art load-locking thrust joint.

FIG. 3 depicts, partly in elevation and partly in vertical section, a load-locking ball joint in accordance with a first embodiment of the present invention.

FIG. 10 is a front view of a surgery microscope suspended in a self-locking ball joint in accordance with the present invention.

DETAILED DESCRIPTION OF THE PREFERRED EMBODIMENTS

Figure 4:
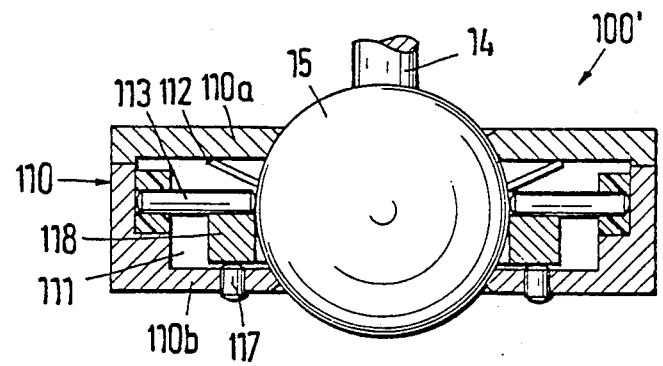
FIG. 4 depicts, partly in elevation and partly in vertical section, a load-locking ball joint with pins as clamping elements acting on the joint ball, in accordance with a second embodiment of the present invention.

In the case of the load-locking ball joint 100 in FIG. 3, a joint ball 15 with a shaped-on hinge pin or rod 14 is mounted in rotary manner in a housing 10, which is formed from two housing parts 10a, 10b. Housing part 10b and joint ball 15 define a conical annular clearance 11 in which balls 13 are pressed by at least one spring 12 to contact joint ball 15 at a point which when joined to the center of joint ball 15 defines an angle $\alpha$ with the horizontal radius of joint ball 15, with $\tan \alpha \leq \mu$, where $\mu$ is the coefficient of friction. Housing part 10b constitutes the bottom of housing 10, with housing part 10a as the upper cover. Balls 13, which have a small diameter compared with joint ball 15 and springs 12, constitute the mechanical clamping elements for the joint ball 15.

On rotating the joint ball 15, balls 13, as the clamping element on one side, are rolled into the conical annular clearance 11 and result in jamming of the joint ball 15 in housing 10. By means of said balls 13, the movement of joint ball 15 in its mounting is prevented, and this is achieved by balls 13 as mechanical elements as a result of the self-locking action achieved.

The clamping elements used can be disengaged from the outside, so that then there is no longer any self-locking action. For this purpose, the balls 13 are supported on a ring 18 arranged in the interior of housing 10 and connected by means of pins indicated at 17 to an operating lever 16, so that with the latter and via pins 17 it is possible to displace ring 18, which presses the balls 13 counter to the tension of spring 12 from their engaging position in the conical annular clearance 11, so that free mobility of the joint balls 15 is obtained.

Balls 13 are distributed in the conical annular clearance 11 formed between joint ball 15 and the cylindrical bore 11a formed in the interior of housing 10. The springs 12 acting on the balls 13 represent the means bringing about the elastic forces.

As high surface pressures occur between the balls 13 and the joint ball 15 in conical annular clearance 11, it is advantageous to use differently constructed, surface pressure-reducing bodies for obtaining self-locking. The embodiments of load-locking ball joints shown in FIGS. 4, 5 and 6, 7 provide possibilities for clamps arranged in rotationally symmetrical manner to the joint ball 15 to bring about the self-locking of the latter.

Figure 5:
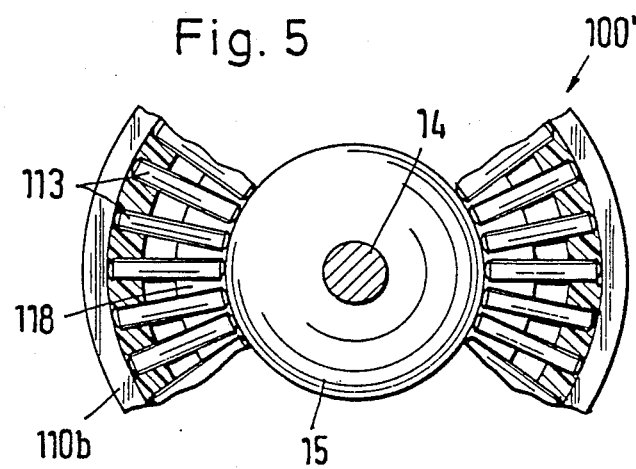
FIG. 5 is a fragmentary top plan view of the ball joint according to FIG. 4.

The load-locking ball joint 100' according to FIGS. 4 and 5 also comprises a housing 110 with the two housing parts 110a, 110b, whereof housing part 110b forms the bottom part and housing part 110a the top cover. The joint ball 15 is arranged in the interior of housing 110. In the interior of housing 110 is also provided an annular clearance 111, which receives a plurality of pins 113, which are supported on their side remote from joint ball 15 on the inner wall face of housing 110 and whose other free ends engage on the surface of joint ball 15 and are supported on a ring 118 in the interior of the housing, which is in operative connection by pins 117 passed through the housing wall and which are in turn connected with an operating lever not shown in FIG. 4 and which is constructed in the same way as operating lever 16 for the load-locking ball joint 100 shown in FIG. 3.

Pins 113 are also subject to the action of springs 112 and together therewith form the clamping elements. Pins 113 are positioned radially round the joint ball 15 in one plane, i.e. positioned on ring 118.

Figure 6:
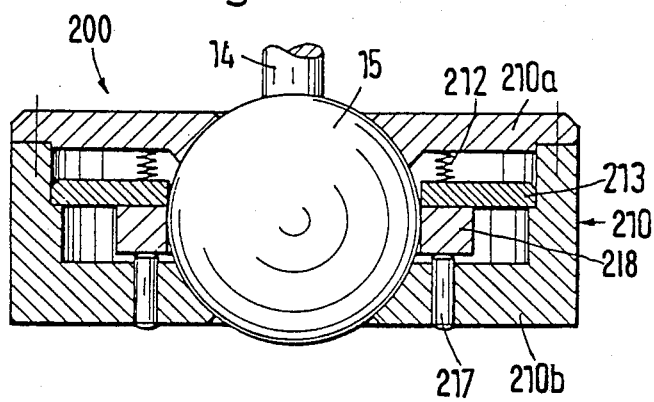
FIG. 6 depicts, partly in elevation and partly in vertical section, a load-locking ball joint with clamping elements in the form of disk segments acting on the joint ball, in accordance with another embodiment of the present invention.
Figure 7:
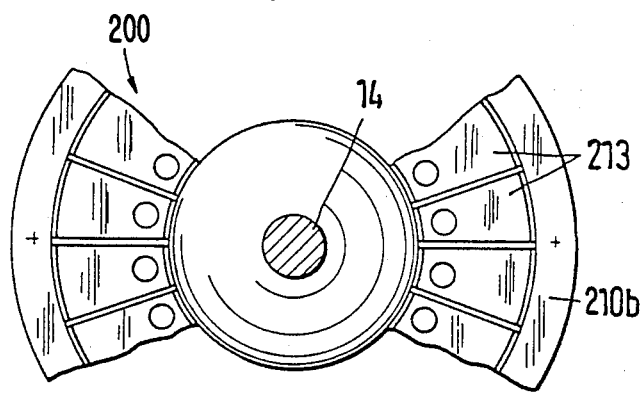
FIG. 7 is a fragmentary top plan view of the ball joint according to FIG. 6.

In the embodiment shown in FIGS. 6 and 7, pins 113 are replaced by a plurality of disk segments 213, which in the same way as pins 113 are arranged in rotationally symmetrical manner around ball joint 15. The construction of the load-locking ball joint 200 according to FIGS. 6 and 7 otherwise corresponds to the embodiment shown in FIGS. 4 and 5. Disk segments 213 are also subject to the action of springs 212. In all embodiments of the load-locking ball joint according to FIGS. 3, 4, 5 and 6, 7, it is advantageous if each clamp is subject to the action of a spring.

The self-locking effect using pins 113 or disk segments 213 as clamping elements is achieved in that the pins or disk segments engage on the outer face of the joint ball 15 and during the rotation of the latter are moved on that surface. However, on the other side they are supported on a fixed bearing surface, in this case the inner wall of the housing, the distance between the point on the joint ball 15 and the support point increases with a slope whose tangent is less than than the friction coefficient.

Also in those cases where pins 113 or disk segments 213 are used as clamping elements in accordance with FIGS. 4, 5 and FIGS. 6, 7, the self-locking action is removed if the clamping elements are disengaged from the outside with respect to springs 12, 112, 212 via pins 17, 117 and ring 18, 118.

Figure 8:
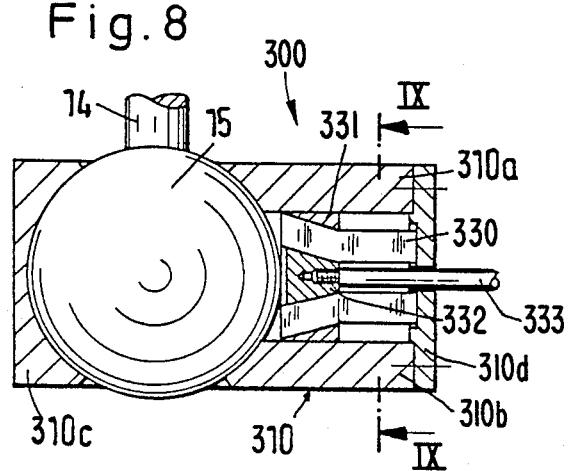
FIG. 8 depicts, partly in elevation and partly in vertical section, a load-locking ball joint with a clamping element acting on one side of the joint ball, in accordance with a further embodiment of the present invention.
Figure 9:
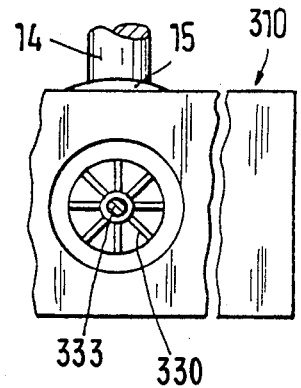
FIG. 9 is a vertical sectional view along line IX—IX of FIG. 8.

In the case of the embodiment of a load-locking ball joint 300 shown in FIGS. 8 and 9, there is once again a joint ball 15 arranged in a housing 310a, 310b the latter comprising two parts 10a, 10b connected by the rear part 310c, whilst forming a recess for receiving joint ball 15. At least one rotationally symmetrical clamp 330 is arranged in a cylindrical recess in housing 310, which can be closed by part 310d. The rotationally symmetrical clamps 330 act on one side on the joint ball 15 mounted in rotary manner in housing 310. Each clamp 330 can be engaged and disengaged with respect to a control member having an internal cone 331 and an external cone 332 via a thrust rod 333, so that self-locking is obtained or prevented.

One example of a use of a load-locking ball joint, 100', 200, 300 is shown in FIG. 10, where a surgery microscope 50 with a microscope suspension mount 15 is suspended on a load-locking ball joint 100a, as described hereinbefore and shown in FIGS. 3 to 9. The operating members, such as operating levers 16 and the thrust rod 33 for releasing the self-locking effect, are preferably located in the vicinity of the operating zone close to the microscope objective and can be simultaneously constructed in such a way that they are used for pivoting the microscope into the correct working position.

What is claimed is:

1. A load-locking joint for pivotally coupling a first object to a second object, said joint comprising:
   a joint ball having extending therefrom a joint pin or rod adapted for attachment to a first object;
   a housing having a bore therein, with said joint ball substantially enclosed in said bore and with said joint pin or rod passing from said housing, the joint ball and the bore defining a conical annular clearance therebetween, said housing adapted for attachment to a second object;
   support means within said bore;
   biasing means with said bore;
   mechanical clamping means having discontinuous portions disposed circumferentially around the joint ball within the bore and supported by said support means; a separate biasing means for different ones of said portions of said mechanical clamping means being effective to normally bias said mechanical clamping means against said joint ball in a clamping position to inhibit relative rotation between said joint ball and said mechanical clamping means, the coefficient of friction between said joint ball and said mechanical clamping means being greater than the tangent of the cone angle of said conical annular clearance; and
   release means for moving said mechanical clamping means from the clamping position against the bias of said biasing means to release said joint ball for relative rotation between said joint ball and said housing.

2. A load-locking joint as claimed in claim 1 wherein said mechanical clamping means comprises a plurality of balls.

3. A load-locking joint as claimed in claim 1 wherein said support means includes a ring member.

4. A load-locking joint as claimed in claim 1 wherein said release means comprises at least one pin member extending through said housing and adapted to be forced against the bias of said spring means to move said mechanical clamping means from the clamping position.

5. A load-locking joint as claimed in claim 4 wherein said release means further comprises a lever pivotally mounted on said housing and pivotal between a release position, in which said lever forces said at least one pin member against the bias of said spring means to move said mechanical clamping means from the clamping position, and a locking position, in which said lever allows said spring means to bias said mechanical clamping means into the clamping position.

6. A load-locking joint as claimed in claim 1 further comprising a surgical microscope attached to one of said joint pin or rod and said housing.

7. A load-locking joint for pivotally coupling a first object to a second object, said joint comprising:
   a joint ball having extending therefrom a joint pin or rod adapted for attachment to a first object;
   a housing having a bore therein, with said joint ball substantially enclosed in said bore and with said joint pin or rod passing from said housing, the joint ball and the bore defining a conical annular clearance therebetween, said housing adapted for attachment to a second object;

support means within said bore;

biasing means with said bore;

mechanical clamping means comprising a plurality of pins within the bore and supported by said support means and said biasing means, with said biasing means normally biasing said mechanical clamping means against said joint ball in a clamping position to inhibit relative rotation between said joint ball and said mechanical clamping means, the coefficient of friction between said joint ball and said mechanical clamping means being greater than the tangent of the cone angle of said conical annular clearance; and release means for moving said mechanical clamping means from the clamping position against the bias of said biasing means to release said joint ball for relative rotation between said joint ball and said housing.

8. A load-locking joint for pivotally coupling a first object to a second object, said joint comprising:

a joint ball having extending therefrom a joint pin or rod adapted for attachment to a first object;

a housing having a bore therein, with said joint ball substantially enclosed in said bore and with said joint pin or rod passing from said housing, the joint ball and the bore defining a conical annular clearance therebetween, said housing adapted for attachment to a second object;

support means within said bore;

biasing means with said bore;

mechanical clamping means comprising a plurality of disk segments within the bore and supported by said support means and said biasing means, with said biasing means normally biasing said mechanical clamping means against said joint ball in a clamping position to inhibit relative rotation between said joint ball and said mechanical clamping means, the coefficient of friction between said joint ball and said mechanical clamping means being greater than the tangent of the cone angle of said conical annular clearance; and release means for moving said mechanical clamping means from the clamping position against the bias of said biasing means to release said joint ball for relative rotation between said joint ball and said housing.

9. A load-locking joint for pivotally coupling a first object to a second object, said joint comprising:

a housing having a bore therein, said housing adapted for attachment to a first object;

an annular support ring within said bore;

a joint ball within the annulus of said support ring and substantially enclosed within said bore, said joint ball having a joint pin or rod extending therefrom, passing from said housing, and adapted for attachment to a second object;

a plurality of mechanical clamping members within said bore and supported by said support ring;

means for biasing different ones of said clamping means independently of others of said clamping means to urge said mechanical clamping members independently in a clamping position against said joint ball to inhibit relative rotation between said joint ball and said housing; and release means for moving said mechanical clamping means from the clamping position against the bais of said biasing means to release said joint ball for relative rotation between said joint ball and said housing.

10. A load-locking joint as claimed in claim 9 wherein said mechanical clamping means comprises a plurality of balls.

11. A load-locking joint as claimed in claim 9 wherein said mechanical clamping means comprises a plurality of pins.

12. A load-locking joint as claimed in claim 9 wherein said mechanical clamping means comprises a plurality of disk segments.

13. A load-locking joint as claimed in claim 9 wherein said release means comprises at least one pin member extending through said housing and adapted to be forced against the bias of said spring means to move said mechanical clamping means from the clamping position.

14. A load-locking joint as claimed in claim 9 wherein said release means further comprises a lever pivotally mounted on said housing and pivotal between a release position, in which said lever forces said at least one pin member against the bias of said spring means to move said mechanical clamping means from the clamping position, and a locking position, in which said lever allows said spring means to bias said mechanical clamping means into the clamping position.

15. A load-locking joint as claimed in claim 9 further comprising a surgical microscope attached to one of said joint pin or rod and said housing.

16. A load-locking joint for pivotally coupling a first object to a second object, said joint comprising:

a housing having a bore therein, said housing adapted for attachment to a first object;

a joint ball substantially enclosed within the bore of said housing and having a joint pin or rod extending therefrom, passing from said housing, and adapted for attachment to a second object;

an internal cone member;

an external cone member;

a rotationally symmetrical clamping member rotatably mounted within said bore between said internal cone member and said external cone member for operation therewith; and a thrust rod connected to said clamp member and extending through said housing and operative to move said clamp member between a clamping position in which said clamp member inhibits relative rotation between said joint ball and said housing and a released position allowing such relative rotation.

17. A load-locking joint for pivotally coupling a first object to a second object, said joint comprising:

a joint ball having extending therefrom a joint pin or rod adapted for attachment to a first object;

a housing having a bore therein, with said joint ball substantially enclosed in said bore and with said joint pin or rod passing from said housing, the joint ball and the bore defining a conical annular clearance therebetween, said housing being adapted for attachment to a second object;

support means within said bore;

biasing means with said bore;

mechanical clamping means having discontinuous portions disposed circumferentially around the joint ball within the bore and supported by said support means; a separate biasing means for different portions of said mechanical clamping means being effective to normally bias said mechanical clamping means against said joint ball in a clamping position to inhibit relative rotation between said joint ball and aid mechanical clamping means, the coefficient of friction between said joint ball and said mechanical clamping means being greater than the tangent of a cone angle of said conical annular clearance, said cone angle being equal to the angle formed by a line passing through the center of the joint ball and a point of engagement of the mechanical clamping means and a line passing through the center of the joint ball that is substantially perpendicular to the direction of movement of said mechanical clamping means; and release means for moving said mechanical clamping means from the clamping position against the bias of said biasing means to release said joint ball for relative rotation between said joint ball and said housing.

* * * * *